United States Patent
Bocquenet et al.

(10) Patent No.: US 6,635,151 B1
(45) Date of Patent: Oct. 21, 2003

(54) LACTAM DEHYDRATION METHOD

(75) Inventors: Gerald Bocquenet, Communay (FR); Yves Courtemanche, Lyons (FR); Patrick Houssier, Pierre-Bénite (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/744,650

(22) PCT Filed: Jul. 15, 1999

(86) PCT No.: PCT/FR99/01732

§ 371 (c)(1),
(2), (4) Date: May 24, 2001

(87) PCT Pub. No.: WO00/06540

PCT Pub. Date: Feb. 10, 2000

(30) Foreign Application Priority Data

Jul. 28, 1998 (FR) .............................................. 98 09808

(51) Int. Cl.$^7$ ........................... B01D 3/00; B01D 201/16
(52) U.S. Cl. .............................. 203/14; 203/2; 203/78; 203/79; 203/80; 203/DIG. 14; 540/540
(58) Field of Search ............................... 203/12, 14, 73, 203/79, 78, 2, 80, DIG. 14, 91–98, 24, 26; 540/540, 538, 539

(56) References Cited

U.S. PATENT DOCUMENTS

| 4,148,793 A | * | 4/1979 | Danziger et al. | ........... 540/540 |
| 4,457,807 A | * | 7/1984 | Rulkens et al. | ................ 203/72 |
| 4,767,503 A | * | 8/1988 | Crescentini et al. | .......... 203/48 |
| 4,892,624 A | * | 1/1990 | Fuchs | ......................... 203/73 |
| 5,458,740 A | * | 10/1995 | Losier et al. | ................. 203/73 |
| 5,693,793 A | | 12/1997 | Ritz et al. | .................... 540/539 |
| 5,700,358 A | * | 12/1997 | Fuchs et al. | .................. 203/78 |

FOREIGN PATENT DOCUMENTS

| EP | 0659741 | 6/1995 |
| GB | 990124 | 4/1965 |
| WO | WO9514664 | 6/1995 |
| WO | WO9514665 | 6/1995 |
| WO | WO9622974 | 8/1996 |

* cited by examiner

*Primary Examiner*—Virginia Manoharan
(74) *Attorney, Agent, or Firm*—Burns, Doane, Swecker & Mathis, L.L.P.

(57) ABSTRACT

The present invention relates to a process for separating the water from an aqueous lactam solution.

It applies more particularly to a mixture resulting from the reaction between an aminonitrile and water (this reaction also being called cyclizing hydrolysis).

The subject of the invention is a process for separating the water from an aqueous lactam solution, which process is economical both from the standpoint of the investment necessary for its implementation and from the standpoint of the operating cost.

10 Claims, No Drawings

LACTAM DEHYDRATION METHOD

The present invention relates to a process for separating the water from an aqueous lactam solution.

It applies more particularly to a mixture resulting from the reaction between an aminonitrile and water (this reaction also being called cyclizing hydrolysis).

During the cyclizing hydrolysis of an aminonitrile in order to form a lactam, one molecule of ammonia per molecule of lactam is also formed. At the end of the reaction, the reaction mixture therefore contains at least the lactam produced, the excess water and ammonia.

It may contain lesser amounts of aminonitrile that has not reacted, or possible by-products of the reaction.

It may also comprise a solvent possibly used in the cyclizing hydrolysis reaction.

The cyclizing hydrolysis may be carried out in vapour phase or in liquid phase. The process of the invention may apply to mixtures resulting from one or other of these methods of preparation.

For the description of the various processes for preparing a lactam by cyclizing hydrolysis of an aminonitrile, reference may be made, for example, to Patent EP-A-0,659,741 or to International Patent Application WO-A-96/22974 or to International Patent Applications WO-A-95/14664 and 95/14665.

The aminonitriles used for preparing lactams are more particularly aminonitriles having from 4 to 12 carbon atoms, preferably linear or branched aliphatic aminonitriles.

As examples of such aminonitriles, mention may be made of those which derive from the hydrogenation of one of the two nitrile functional groups of dinitriles, such as adiponitrile, methylglutaronitrile, ethylsuccinonitrile, dimethylsuccinonitrile, succinonitrile, glutaronitrile and dodecanedinitrile, into a primary amine functional group.

Among the solutions resulting from the cyclizing hydrolysis of an aminonitrile into a lactam, those which correspond to the preparation of caprolactam from 6-aminocapronitrile and water are the most important from an industrial standpoint, since the said caprolactam, upon polymerization, leads to nylon-6.

The process of the invention will therefore relate more particularly to the distillation of the water from aqueous solutions of caprolactam, but this distillation may also be transposed to aqueous solutions of other lactams.

It is necessary beforehand to have separated, generally by distillation, the ammonia formed in the reaction.

One method of separating the water that may be envisaged consists in distilling the water at reduced pressure (less than or equal to 20 mbar absolute, for example) so as not to exceed 145° C. at the bottom of the column.

Such a process involves condensing the water thus distilled, by circulating a fluid (such as water) at a temperature of less than or equal to 15° C. By way of example, this requires the presence of a refrigeration unit having a power of approximately 1.2 megawatts in order to treat the order of 8 tonnes/hour of an aqueous lactam solution having a solutes concentration of approximately 60% by weight.

The subject of the present invention is a process for separating the water (which process may also be called dehydration) from an aqueous lactam solution, which process is more economical both from the standpoint of the investment necessary for its implementation and from the standpoint of the energy consumed.

More specifically, it consists of a process for separating the water from an aqueous lactam solution, characterized in that:

the water is distilled in a first distillation column by maintaining a temperature at the bottom of the column less than or equal to 160° C. and preferably less than or equal to 145° C., and at an absolute pressure of 50 millibars to 200 millibars, the distillate being condensed at a temperature of 30° C. to 60° C. using a coolant system;

the lactam remaining at the bottom of the column is then subjected to a distillation in a second distillation column by maintaining a temperature at the bottom of the column less than or equal to 160° C. and preferably less than or equal to 145° C., and at a pressure of 10 to 45 millibars, so as to separate the water that it still contains;

the water, containing traces of lactam, distilled in the second column, is recovered in the form of vapour at a temperature greater than or equal to 70° C.

By operating the process according to the invention, it is not necessary to have a refrigeration unit for condensing the water at the top of the first column.

The water, containing traces of lactam, distilled in the second column is preferably recycled into the first distillation column. This recycling may be carried out after condensing the water at the pressure of the second column, either between 10 and 45 millibars absolute, corresponding to a temperature of 5° C. to 30° C. However, such a variant only requires a refrigeration unit having a power of approximately 100 to 200 times less than that of the refrigeration unit which would have been necessary in the context of a distillation using a single column.

According to another embodiment of the invention, the water containing traces of lactam, distilled in the second column may be compressed by means of a steam ejector to a pressure allowing it to condense at a temperature greater than 15° C., using a standard coolant such as the atmospheric air or water at room temperature. In this case, the delivery pressure of the steam ejectors must be at least equal to the pressure of the first column, advantageously between 25 millibars absolute and 50 to 200 millibars absolute, the pressure of the first column. In this embodiment, the refrigeration units are omitted.

Overall, the present process is characterized, for the same capacity of distillation of an aqueous lactam solution, by a much lower total energy consumption which can be broken down into an electricity consumption which is 100 to 200 times less, as indicated previously, and an additional energy consumption in the form of steam, in order to heat the second column, which represents only less than approximately 15% of the electrical energy saving made.

The water recovered from the top of the first column is condensed at the pressure of this column, i.e. between 50 millibars and 200 millibars corresponding to a temperature of between 35 and 60° C., compatible with most coolants generally used, such as atmospheric air or river water or water from cooling towers.

The water recovered from the top of the second column may be partially condensed at approximately 70° C. before being completely condensed and then returned to the first column. This arrangement makes it possible to limit the amount of water to be condensed under particular conditions and therefore to reduce the amount of energy necessary for carrying out this operation.

Before this condensed water is recycled into the first column, it may be advantageous to add a certain amount of water in order to reduce the caprolactam concentration and to prevent it from precipitating.

Furthermore, despite the need for an additional column, the investment necessary, for the same production, is also less in the process according to the invention than in a process carried out using a single column, on account of the considerable refrigerating capacity needed in this latter process.

The aqueous lactam solution, preferably caprolactam, from which the ammonia has been removed, has a lactam concentration which varies widely depending on the conditions under which the said lactam is prepared, especially the initial water/aminonitrile molar ratio and whether or not an organic solvent is present. The lactam concentration may generally vary from 5% to 80% by weight with respect to the total weight of the solution, and preferably from 20% to 75%.

Since the water to be distilled has physical properties that are very different from the lactam from which it must be separated, it is not necessary to use distillation columns having a very large number of theoretical trays.

Columns, particularly packed columns, with at least two theoretical trays are very suitable for implementing the process of the invention. Columns having a number of theoretical trays ranging from 2 to 10 may, for example, be used. The packing used may be of the loose packing or ordered packing type, as proposed by the various manufacturers and sized according to the rules of the art. It is also possible to use columns with trays of the same efficiency, although this is less advantageous from the standpoint of head losses.

The process of the invention does not exclude the possibility of separating the water from the aqueous lactam solution using more than two columns.

However, in general this is unnecessary and, furthermore, the economic advantages provided by the process described above would be fewer if the number of distillation columns were to be increased significantly. The examples which follow illustrate the invention.

EXAMPLE 1

Distillation with Two Columns in Series Operating at Different Pressures

Distillation of an aqueous caprolactam solution having the following composition:
water: 40% by weight
caprolactam: 60% by weight.
The characteristics of the first distillation column are as follows:
number of distillation stages (theoretical trays): 4
reflux ratio: 0.1
absolute operating pressure at the top of the column: 0.13 bar
top temperature: 50° C.
bottom temperature: 135° C.
heat load of the boiler: 3.9 Gcal/h
heat load of the condenser: 3.6 Gcal/h.
The characteristics of the second distillation column are as follows:
number of distillation stages (theoretical trays): 3
absolute operating pressure at the top of the column: 0.025 bar
top temperature: 130° C.
bottom temperature: 145° C.
heat load of the boiler: 0.08 Gcal/h
heat load of the 70° C. -moderated partial condenser: 0.02 Gcal/h
heat load of the condenser for the water to be recycled into the first column: 0.02 Gcal/h power consumed by the refrigeration unit in order to condense the water at the top of the second column: 10 kW, with condensation at 35° C.

The caprolactam, stripped of its water, which was obtained in this example has the following composition:
water: 0.010% by weight
caprolactam: 99.990% by weight.

Comparative Test

Conventional Distillation Using a Refrigeration Unit at the Top of the Column

Distillation of a product having the following composition:
water: 40% by weight
caprolactam: 60% by weight.
The characteristics of the distillation column are as follows:
number of distillation stages: 4
reflux ratio: 0.1
absolute operating pressure at the top of the column: 0.015 bar
top temperature: 13° C.
bottom temperature: 140° C.
heat load of the boiler: 3.6 Gcal/h
heat load of the condenser: 3.4 Gcal/h
power consumed by the refrigeration unit: 1200 kW, with condensation at 35° C.

The caprolactam, stripped of its water, which was obtained in the comparative test has the following composition:
water: 0.004% by weight
caprolactam: 99.996% by weight.

What is claimed is:

1. A process for separating water from an aqueous lactam solution, consisting essentially of:

distilling the aqueous lactam solution in a first distillation column while maintaining a temperature at the bottom of the column less than or equal to 160° C. and at an absolute pressure of 50 millibars to 200 millibars, distillate recovered from the top of the column having been condensed at a temperature of 30° C. to 60° C. using a coolant;

forwarding the lactam solution remaining at the bottom of the first distillation column to a second distillation column and maintaining a temperature at the bottom of the second distillation column less than or equal to 160° C. and at a pressure of 10 millibars to 45 millibars;

recovering water, containing traces of lactam, at the top of the second column, as vapor at a temperature greater than or equal to 70° C.

2. The process according to claim 1, wherein the temperature maintained at the bottom of the first column is less than or equal to 145° C.

3. The process according to claim 1, wherein the temperature maintained at the bottom of the second column is less than or equal to 145° C.

4. The process according to claim 1, wherein the aqueous lactam solution is obtained by the cyclizing hydrolysis of 6-aminocapronitrile and the lactam is caprolactam.

5. The process according to claim 1, wherein the water vapor containing traces of lactam, recovered in the second column, is recycled into the first column.

6. The process according to claim 5, wherein the water vapor is recycled after condensing it at a temperature of 5° C. to 30° C. at a pressure of 10 to 45 millibars.

7. The process according to claim 5, wherein the water containing traces of lactams is recycled after compressing the distilled water at a pressure at most equal to the pressure of the first column and condensing at a temperature greater than 15° C.

8. The process according to claim 5, wherein water is added to the water containing traces of lactam, which is recovered in the second column, before it is recycled into the first column.

9. The process according claim 1, wherein the first distillation column and the second distillation column each have at least two theoretical trays.

10. The process according to claim 1, wherein the distillation columns are packed columns.

* * * * *